United States Patent
Lenz

(10) Patent No.: US 7,479,128 B1
(45) Date of Patent: Jan. 20, 2009

(54) PROTECTIVE COATINGS FOR MEDICAL DEVICES

(75) Inventor: Jason T. Lenz, Maplewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 09/477,236

(22) Filed: Jan. 4, 2000

(51) Int. Cl.
*A61M 5/32* (2006.01)

(52) U.S. Cl. .................................. 604/265

(58) Field of Classification Search ............. 604/265, 604/264, 523, 96, 101, 102, 103, 172, 280, 604/96.01, 101.01–101.05, 915, 916, 381, 604/382, 46; 606/191–194
See application file for complete search history.

(56) References Cited

U.S. PATENT DOCUMENTS

| | | | |
|---|---|---|---|
| 4,490,421 A | 12/1984 | Levy | 428/35 |
| 4,702,252 A * | 10/1987 | Brooks et al. | 128/344 |
| 5,041,100 A | 8/1991 | Rowland et al. | 604/265 |
| 5,061,424 A | 10/1991 | Karimi et al. | 264/171 |
| 5,077,352 A * | 12/1991 | Elton | 525/409 |
| 5,100,381 A | 3/1992 | Burns | 604/96 |
| 5,135,381 A | 8/1992 | Evans | 604/8 |
| 5,135,474 A | 8/1992 | Swan et al. | 604/265 |
| 5,304,121 A * | 4/1994 | Sahatjian | 604/53 |
| 5,348,538 A | 9/1994 | Wang et al. | 604/96 |
| 5,383,806 A | 1/1995 | Prater | 446/220 |
| 5,423,745 A | 6/1995 | Todd et al. | 604/53 |
| 5,487,730 A | 1/1996 | Marcadis et al. | 604/96 |
| 5,490,839 A * | 2/1996 | Wang et al. | 604/96 |
| 5,496,276 A | 3/1996 | Wang et al. | 604/96 |
| 5,503,631 A | 4/1996 | Onishi et al. | 604/96 |
| 5,556,383 A | 9/1996 | Wang et al. | 604/96 |
| 5,613,979 A | 3/1997 | Trotta et al. | 606/194 |
| 5,653,690 A * | 8/1997 | Booth et al. | 604/103.07 |
| 5,693,014 A | 12/1997 | Abele et al. | 604/96 |
| 5,693,088 A | 12/1997 | Lazarus | 623/1 |
| 5,714,110 A | 2/1998 | Wang et al. | 264/529 |
| 5,720,726 A | 2/1998 | Marcadis et al. | 604/96 |
| 5,720,735 A | 2/1998 | Dorros | 604/284 |
| 5,738,901 A | 4/1998 | Wang et al. | 427/2.3 |
| 5,743,963 A | 4/1998 | Williamitis et al. | 118/680 |
| 5,746,745 A | 5/1998 | Abele et al. | 606/108 |
| 5,766,158 A | 6/1998 | Opolski | 604/265 |
| 5,766,204 A * | 6/1998 | Porter et al. | 606/198 |
| 5,773,081 A | 6/1998 | Williamitis et al. | 427/211 |
| 5,797,877 A | 8/1998 | Hamilton et al. | 604/96 |
| 5,830,182 A | 11/1998 | Wang et al. | 604/96 |
| 5,853,481 A | 12/1998 | Williamitis et al. | 118/679 |
| 5,860,998 A | 1/1999 | Robinson et al. | 606/194 |
| 5,863,614 A | 1/1999 | Williamitis et al. | 427/429 |
| 5,868,779 A | 2/1999 | Ruiz | 606/194 |
| 5,876,374 A | 3/1999 | Alba et al. | 604/96 |

(Continued)

FOREIGN PATENT DOCUMENTS

EP 380 102 8/1990

(Continued)

*Primary Examiner*—Manuel A Mendez
(74) *Attorney, Agent, or Firm*—Vidas, Arrett & Steinkraus, PA

(57) ABSTRACT

This invention relates to a method of providing a coating on a medical device, especially a dilatation balloon, which improves the durability of the balloon.

14 Claims, 4 Drawing Sheets

U.S. PATENT DOCUMENTS 6,010,480 A * 1/2000 Abele et al. ............ 604/103.06
6,176,849 B1 * 1/2001 Yang et al. .................. 604/265
6,273,878 B1 * 8/2001 Muni .......................... 604/265

FOREIGN PATENT DOCUMENTS

| EP | 0 872 253 A2 | 10/1998 |
|---|---|---|
| WO | 94/27665 | 12/1994 |
| WO | 95/33422 | 12/1995 |
| WO | 99/59649 | 11/1999 |

* cited by examiner

PROTECTIVE COATINGS FOR MEDICAL DEVICES

FIELD OF THE INVENTION

This invention relates to a method of providing a coating on a medical device, especially a dilatation balloon, which improves the durability of the device.

BACKGROUND OF THE INVENTION

Catheter devices having an inflatable balloon mounted at the distal end are useful in a variety of medical procedures such as coronary angioplasty, stent delivery and placement for the opening of occluded or blocked blood vessels, for urological and reproductive surgeries, and to deliver biologically compatible fluids, such as radiologically opaque fluid for contrast x-rays to precise locations within the body. These procedures often involve the insertion of the device into blood vessels of extremely reduced diameter for long distances through the vascular system. These applications require thin walled high strength balloons of a relatively inelastic or non-compliant nature that have predictable inflation properties.

Once the balloon is positioned at the desired location, it is inflated by supplying liquid under pressure through an inflation lumen to the balloon. The inflation of the balloon causes stretching of a blood vessel, for instance, to reestablish acceptable blood flow through the blood vessel.

Balloon catheters are therefore produced from materials that can withstand high pressure, even at very low film thicknesses. The strength of the material is determined by measuring the tensile strength, and films with high strength relative to film thickness are chosen. Examples of materials useful in balloon catheters include polyethyleneterephthalate (PET); polyether-polyester block copolymers such as the Hytrel® series of block copolymers, also referred to as thermoplastic polyester elastomers, available from Du Pont in Wilmington, Del. or the Arnitel® series available from DSM, the Netherlands, such as Arnitel® 540; and polyamide/polyether/polyesters such as PEBAX® 6333, 7033 and 7233. However, films produced from such materials tend to be harder, and to be scratch and puncture sensitive.

Scratches, abrasions, and even punctures can occur during handling and storage of the devices, or during use. Stents or other objects may scratch or puncture the balloon. Friction between the device and the vessel through which it is being passed can result in failure of the balloon at the weakened points that result from scratches, abrasions or punctures. Lubricious coatings can reduce the friction between the device and the vessel wall, but provides only limited protection and does not really address the problem of scratches, abrasions and punctures. These coatings improve the success rate by altering the coefficient of friction between the device and the vessel wall, but do not address the scratch and puncture resistance other than by building film thickness.

Balloon failure at points of abrasions, scratches or punctures can be a problem during inflation. The balloon may prematurely burst, or the point at which the abrasion, scratch or puncture is located tends to be weaker, and when inflated, will have a tendency to over expand at that point, leading to over extension or bulging in the balloon wall at the weakened point. These bulges can in turn cause damage to blood vessels, for instance. Over inflation is also a problem during stent delivery.

More compliant materials tend to be more scratch and puncture resistant, but do not provide the strength required to withstand the pressures used in some of these procedures. Non-compliance which is the ability to resist expansion beyond a predetermined size upon pressure, and to substantially maintain a profile, is required for balloon catheters, especially those utilized in small vessels. Excessive expansion of more compliant materials can result in the rupture or dissection of blood vessels.

There is a continuing need in the medical device area to provide improved protective layers or coatings to balloons formed of noncompliant materials to increase the resistance of such balloons to scratches, abrasions and punctures. These improved coatings provide increased resistance by building film thickness, but they do not address the issue of what occurs in the event that the balloon is scratched, abraded or punctured.

Efforts have been made to coat a balloon with a continuous coating of a thin durable material. The problem associated with such continuous coatings in that if a pinhole is present in the underlying balloon material, as the balloon is inflated, the coating will also inflate, and at the point of the pinhole, can separate from the balloon material and form a bubble which can dissect an artery or vessel.

Specific examples of such problems occur with oriented PET which is commonly used for forming catheter balloons by a stretch blow molding method. The PET can exhibit pinholes that emit a high-velocity jet of inflation fluid during inflation. This then will result in the bulge forming in the outer coating layer which can cause artery dissection. Pet also exhibits low tear resistance and does not take a crease.

One such method of improving the scratch or abrasion resistance of medical apparatuses is found in U.S. Pat. No. 5,766,158 issued Jun. 16, 1998 to Opolski which describes a protective surface coating for a medical device which contains a matrix polymer and a reinforcing agent to decrease the sensitivity of the medical apparatus to injuries, such as scratches, punctures, and the like. The reinforcing agent is lamellar, platelet, or fiber-like in structure and has a higher surface hardness that the surface hardness of the medical apparatus.

SUMMARY OF THE INVENTION

It is an object of the present invention to provide a protective coating which improves the durability of a medical device, especially a dilatation balloon, and also addresses the problems which can arise if a scratch, abrasion or puncture occurs in, for instance, a balloon wall. The coating is noncontinuous in nature, thus preventing bubbling or aneurysms in the outer protective coating if the underlying device, i.e. balloon wall, becomes damaged and allows inflation medium to escape.

The present invention further relates to a method of providing a dilatation balloon with improved durability comprising the steps of forming a balloon and applying a noncontinuous protective coating to said balloon. The coating comprises a polymeric material which gives the balloon improved durability.

The pattern of the coating may be a "waffle" pattern, a "strip" pattern, or a pattern having circular perforations, or any other pattern of a discontinuous nature.

DETAIL DESCRIPTIONS OF THE PREFERRED EMBODIMENTS

The present coating may be utilized on any medical device which can be damaged by scratching, abrasions, and/or punctures, especially catheter devices, and in particular, balloon catheters or dilatation balloons.

Figure 1:
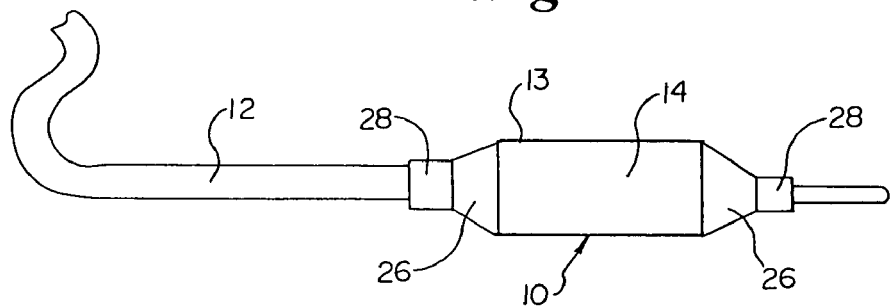
FIG. 1 is a perspective view of a standard dilatation balloon in an uncoated condition.

A dilatation balloon of the present invention is illustrated generally at 10 in FIG. 1, and includes an inflatable balloon 14 mounted at the distal end of an elongated flexible shaft 12. Balloon 14 has a balloon wall 13; Except as noted herein, catheter 10 is conventional in its construction, providing a lumen communicating with the interior of the balloon 14, for inflation and deflation of the balloon, and other optional features conventional in the dilatation catheter art. The balloon 10, has an inflated configuration, illustrated in FIG. 1 and is made up of three main portions: the body 14, the cones 26 and the waist portions 28. Balloon catheters of this type are described in U.S. Pat. No. 5,490,839 to Wang et al. issued Feb. 13, 1996 and herein incorporated by reference.

Figure 2:
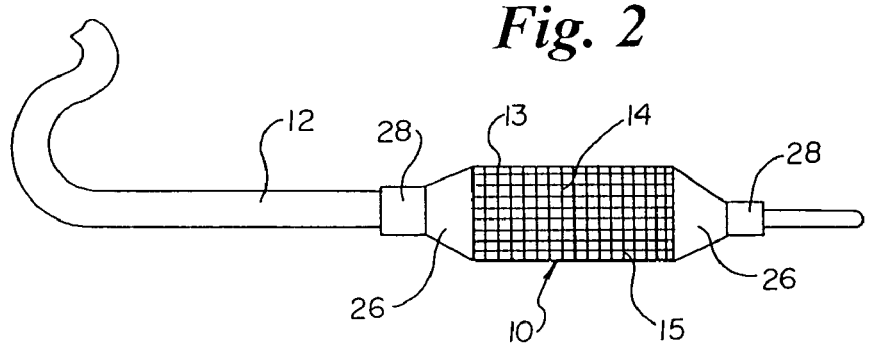
FIG. 2 is a perspective view of a standard dilatation balloon with a "waffle" pattern coating of the present invention.

FIG. 2 illustrates the same balloon 14 coated with a "waffle" pattern coating 15 of the present invention coated over balloon wall 13.

Figure 3:
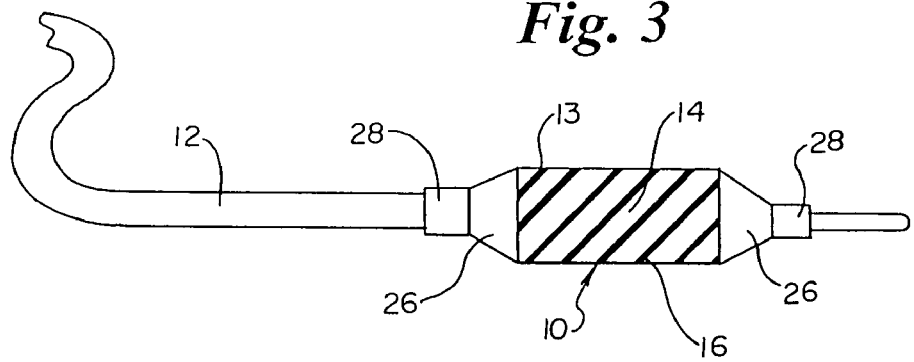
FIG. 3 is a perspective view of a standard dilatation balloon with a "stripe" pattern coating of the present invention.

FIG. 3 illustrates the same balloon construction with another embodiment of the coating 16 of the present invention having a different pattern than that exhibited in FIG. 2. The pattern in this diagram is a "stripe" pattern wherein the stripes run diagonally around the circumference of the balloon.

Figure 4:
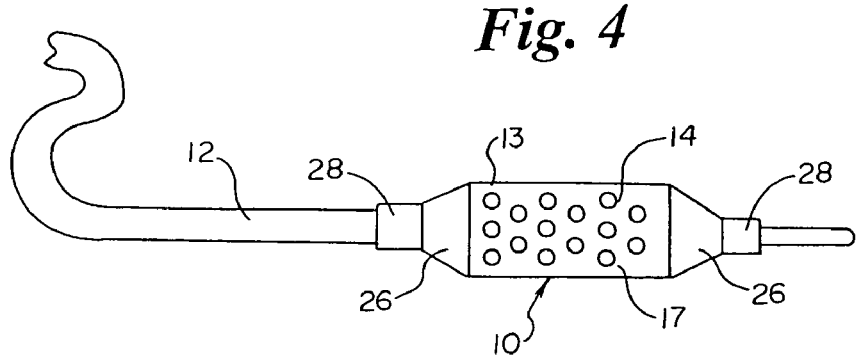
FIG. 4 is a perspective view of a standard dilatation balloon with a substantially solid coating having a uniform pattern of circular perforations.

FIG. 4 illustrates the same balloon construction as in FIGS. 2 and 3 with yet another embodiment of a the coating 17 of the present invention having yet a different pattern than exhibited in the other figures. This embodiment illustrates a more solid coating which has circular perforations spaced at a uniform distance from one another. The size of the perforations may be varied.

Figure 5:
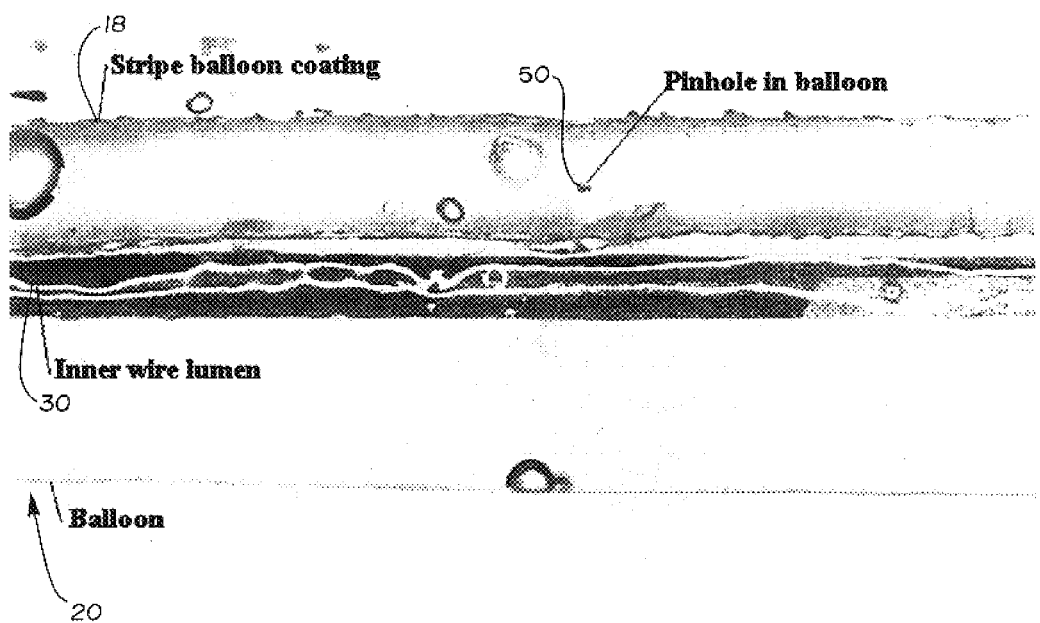
FIG. 5 is a perspective view of a standard dilatation balloon having another embodiment of a "stripe" pattern coating and in an uninflated state.

FIG. 5 illustrates a balloon 20 in its uninflated state, and having a "stripe" pattern coating 18 of a polyurethane polymer, also referred to as a "shape memory polymer." This pattern of has the stripes running longitudinally with the balloon whereas the pattern illustrated in FIG. 3 exhibits stripes running diagonally around the circumference of the balloon 20. The polyurethane polymer utilized in this embodiment is available from Mitsubishi Heavy Industries, Ltd in Tokyo, Japan, under the tradename of SMP-3510. The balloon 20 has an inner wire lumen 30 for delivery of the inflation media. The balloon exhibits a pinhole 50 left of center and beneath a coated section of the balloon.

Figure 6:
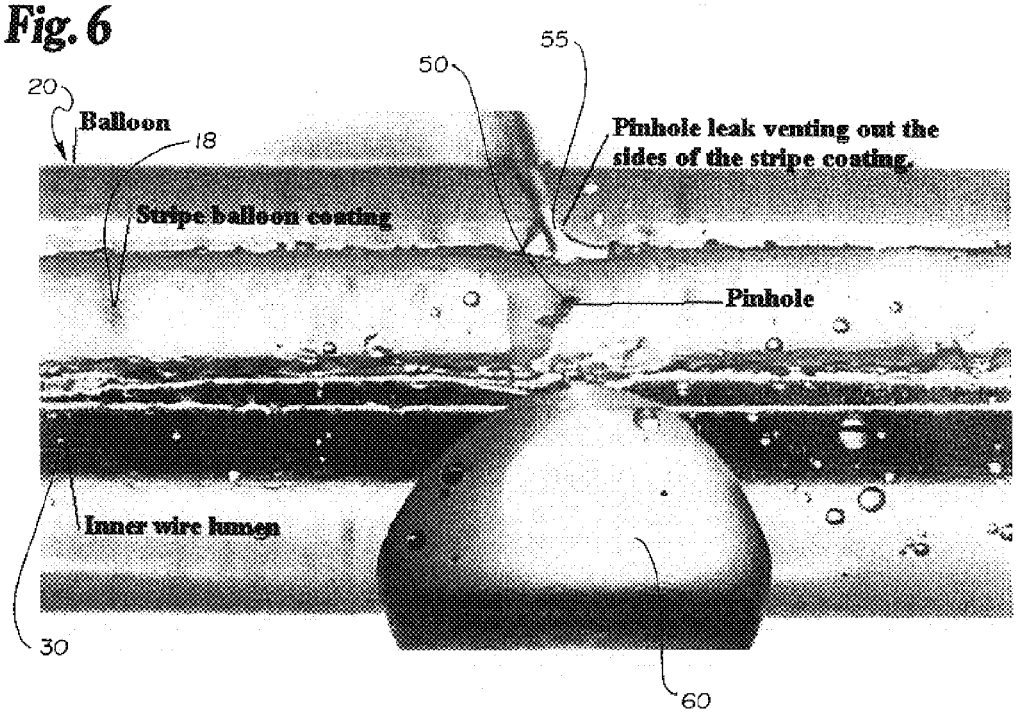
FIG. 6 illustrates the same balloon as shown in FIG. 5 but now having pressure applied as during inflation. No aneurysm is exhibited.

FIG. 6 illustrates the same balloon 20 as shown in FIG. 5 during inflation. Inflation medium can be seen venting from out the edges of the coated section. Desirably, no aneurysm is formed in the coating because the inflation medium can easily escape. The inflation media 55 is exiting through the pinhose 50 and can be seen venting out the sides of the discontinuous stripe coating 18 on balloon 20. The large inverted water droplet 60 seen in the center from of the photograph is forming as a result of the inflation media 55 flowing out of the pinhole 50. Both the stream of inflation media 55 and the droplet 60 are on the same side of the balloon 20. Such droplet formation would not be exhibited were the balloon in an aqueous environment such as a vessel of a patient but such fluid would be carried away in the blood.

Figure 7:
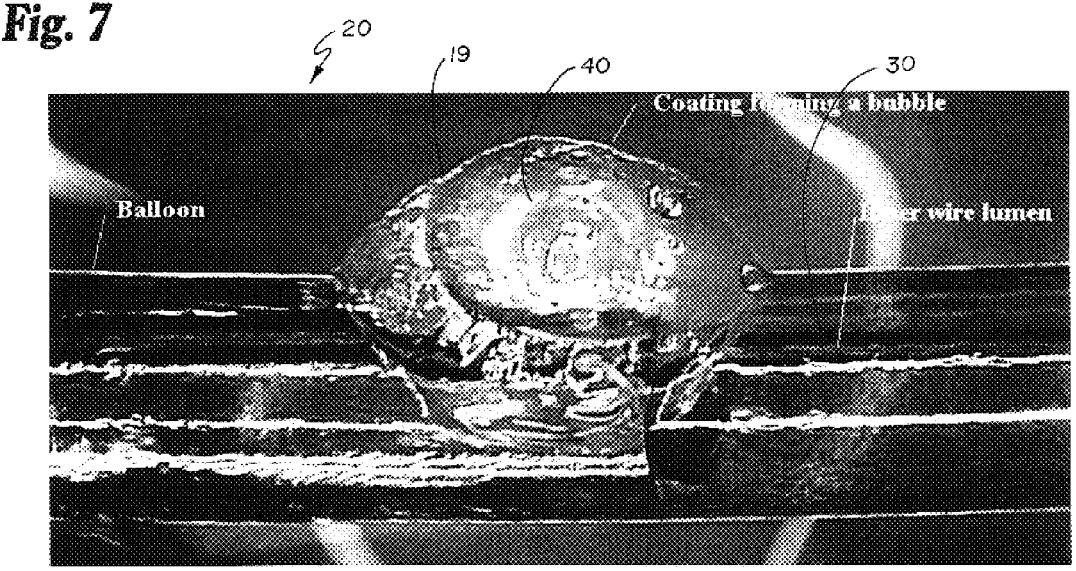
FIG. 7 illustrates a balloon having a continuous coating of polyurethane polymer in its inflated state. An aneurysm is formed in the coating.

FIG. 7 illustrates a balloon 20 having a continuous coating 19 of polyurethane polymer, SMP-3510, available from Mistubishi Heavy Industries, Ltd, in its inflated state. An aneurysm 40 is formed in the coating. Inner wire lumen 30 is for inflation media delivery.

While these are some suggestions as to types of patterns that may be used in the coating method, there are a limitless variety of patterns and sizes of patterns that may be utilized to achieve the objectives of the present invention. Any pattern wherein there is discontinuity in the coating, may alleviate the formation of pinholes which may ultimately lead to aneurysms in the balloon construction, and to damage to the patients vessels.

The balloons may be constructed of thermoplastic polymeric materials including thermoplastic elastomers, i.e. block copolymers; copolymers and terpolymers of ethylene; homopolymers, copolymers and terpolymers of propylene; ethylene α-olefins; polyesters; polyamides; polyurethanes; polycarbonates, vinyl copolymers; ionomer materials and so forth. More specifically, materials such as nylon, Selar®, polyether-polyester block copolymers (i.e. Hytrel® from DuPont or Arnitel® from DSM, Netherlands), Pebax® (polyether block amide copolymers), Surlyn®, polyethylene terephthalate, polytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters or other similar extrudable thermoplastic, polymeric materials, or composites thereof may be utilized in the present invention. Thermosetting materials such as polyimides may also be utilized.

The balloon wall may be noncompliant or compliant. Noncompliant balloons are formed from relatively stiff materials including polyethyleneterephthalate (PET), high density polyethylene, polyamides, polycarbonates and stiff polyurethanes, and so forth. The balloon wall may also be compliant and made of materials such as polyvinyl chloride, polyethylene, polyester copolymers, polyolefin copolymers and so forth. The present invention provides a particular advantage when the balloon wall is made of a stiff, noncompliant material. Such materials tend to scratch more easily, especially if a fold occurs in the balloon.

Some specific preferred balloon materials include polyether block amides, such as Pebax® 7033 or 7233; polyester block ethers such as Arnitel® EM 40; polyethylene terephthalate (0.64 to 0.8 IV PET); and nylon. The formation of catheter balloons made of block copolymer elastomers where the hard segments are polyester or polyamide and the soft segments are polyether, is discussed in U.S. Pat. No. 5,556,383 issued Sep. 17, 1996 to Wang et al. herein incorporated by reference. The formation of catheter balloons made of PET is discussed in U.S. Pat. No. 5,714,110 issued Feb. 3, 1998 to Wang et al. herein incorporated by reference. The formation of catheter balloons produced from block copolymer elastomers is discussed in U.S. Pat. No. 5,830,182 issued Nov. 3, 1998 to Wang et al., herein incorporated by reference.

A typical method of balloon formation involves first extruding a tubular preform, and subsequently blowing the tubular preform into a balloon. The balloon has what is referred to as a body, at least one cone portion, and at least one waist portion.

Suitable balloon forming techniques which may be employed are well known in the art and may be carried out in any conventional manner with conventional extrusion and blowing techniques. Such techniques for balloon formation are discussed in U.S. Pat. No. 4,490,421 to Levy and in U.S. Pat. No. 5,348,538 issued Sep. 20, 1994 to Wang et al. herein incorporated by reference.

The balloon has a coating over the balloon wall. Preferably, the coating will be on the balloon body. However, the cones and the waist portion(s) may also be coated. Any thermoplastic polymeric material which is dissolvable in solvent, and which improves the durability of the balloon may be utilized. The coating polymer is desirably sufficiently flexible and elastic at body temperature and has only a minor, if any, impact on the compliance characteristics of the balloon. The coating material preferably does not adversely affect the compliance characteristics of the balloon itself. The polymeric coating may also preferably have some surface tack for certain applications including stent delivery catheters. A certain amount of tack may help hold the stent more securely when the stent is in the crimped down position.

The polymers may be thermoplastic or thermoset polymeric materials. Thermoplastic materials useful to the present invention include any type of material from which the balloons themselves may be produced, as well as many others. Examples of such materials include vinyl polymers, fluorinated and chlorinated polymers, polyolefins, polyurethanes, polystyrene, polyesters, nylons, polyamides, polycarbonates, polyacrylates, poly(meth)acrylates, copolymerized versions, and so forth. Rubbery block copolymers include those having the general configuration of linear, radial, star, Y-block, multi-block and so forth.

More specifically, the coating material may include polyvinyl chloride; polyethylene terephthalate; polyethylene homopolymers; styrene-butadiene-styrene block copolymers; styrene-ethylene/butylene-styrene block copolymers; styrene-ethylene/propylene-styrene block copolymers; styrene-isoprene-styrene block copolymers; polyester elastomers, polyether-block amides; copolymers of ethylene and vinyl acetate, n-butyl acrylate, methylacrylate; interpolymers of ethylene and at least one alpha-olefin; and so forth.

A preferred class of thermoplastic polymers useful for the coating are the thermoplastic polyurethane polymers.

Thermosetting polymers have functional moieties which are capable of crosslinking with other functional moieties.

Thermosetting materials include polyurethanes formed from an isocyanate and a polyol; acrylics; acrylates; methacrylates; epoxies; unsaturated polyesters; silicones having hydrolyzable acetate groups; polysulfides; cyanoacrylates; formaldehydes condensed with urea, phenol, resorcinol, melamine for instance, and so forth. Thermosetting compositions refer to crosslinkable compositions, even those that do not necessarily require elevated temperatures to initiate the chemical reaction. It is preferable to the present invention to initiate polymerization or cure using electron beam or ultraviolet radiation.

In a preferred embodiment of the present invention, a polyurethane polymer is utilized. The glass transition temperature of these polyurethane polymers may be adjusted by changing the molar ratio of diisocyanate, polyol and chain extender. Glass transition temperatures may also be varied by changing the polyol itself. An example of a polyurethane polymer is SMP-3510 available from Mitsubishi Heavy Industries, Ltd. These polymers are also referred to as "shape memory polymers."

Water based polymers may also be utilized including polyurethane dispersions and emulsion polymers such as acrylics, vinyl acetate homopolymers, vinyl acrylic copolymers, vinyl acetate ethylene copolymers, and so forth. A preferable water base coating is a urethane.

The coating of the present invention is a noncontinuous coating and may be referred to as a porous coating or pattern coating. Pattern coating can be achieved in a number of ways including roll coating, screen printing, pad printing, spraying and so forth. In pad, roll or screen printing, the coating application head, i.e. roll or pad, for instance, will have dimples or indentations which result in a noncontinuous coating being applied to the balloon. The pattern is preferably substantially uniform.

A preferable coating pattern which may be obtained using a pad printing method may be referred to as a waffle pattern wherein the shape of the indentation may be any shape provided the repeating pattern is substantially uniform. Typical indentation shapes are square or round. Such a pattern may be found in FIG. 2 or FIG. 3.

Spraying may also be employed to achieve a pattern type of coating to the balloon but will result in a much less uniform noncontinuous coating.

In the case of thermoplastic polymers, it will be preferable to first dissolve the polymer in a solvent or a blend of solvents prior to applying the coating to the balloon. Suitable solvents include acetone, methyl acetate, dimethylacetate, ethyl acetate, dioxane, alcohols, chloroform, methylene chloride, acetonitrile, toluene, methyl ethyl ketone, tetrahydrofuran, dimethylformamide, dimethylsulfoxide, cyclohexanone, acetates including butyl acetate, dimethylacetate, 1-methoxy-2-propanolacetate, and so forth, and mixtures thereof. The polymer may usually be dissolved in the solvent by shaking or by stirring at room temperature, but if necessary, an elevated temperature, such as about 40-50° C., may be utilized to dissolve the polymer. The coating thickness on the balloon may be adjusted by changing the concentration of the polymer solution. Typically, the concentration of polymer in solution will be about 1% to 60%, more preferably about 5% to about 55%, and most preferably about 10% to 50%. The concentration of the polymer in solution to some degree depends on the particular application with which the medical device will be coated. Some applications require lower viscosity solutions than others. For instance, spray applications may require polymer concentrations of about 10% to about 20% while pad printing may require higher polymer concentrations of about 20% to about 50%.

The solvent is then desirably evaporated from the coating, leaving only the polymer remaining. This may be accomplished either at ambient temperatures, or the evaporation process by be accelerated by drying at elevated temperatures.

Thermoplastic polymers become molten and flowable when subjected to heat. However, the polymers useful to the present invention preferably have high tensile strength. Such high strength polymers also typically have high molecular weights and would require quite high temperatures of over 150° C. to lower the viscosity enough to apply using conventional coating techniques. The balloon materials, being in thin film, would be sensitive to such high temperatures and it would therefore be detrimental to apply the coating to the balloon with high temperatures.

The coating is preferably applied when the balloon is in its inflated state. Coverage of the coating is preferably limited to the body of the balloon, and is not found on the waist or cone portions of the balloon. A particularly preferred method of application is pad printing. The pads are typically formed from a soft silicone rubber. Such materials would have less of a tendency to cause any abrasions in the balloon material. The pad picks up the image or pattern to be printed from an etched plate, and then transfers the coating pattern to the balloon. Using this method, the coating may be wrapped around curved surfaces easily. The shape and design of the pattern can be easily varied. One preferred pattern may be referred to as a "waffle" pattern in which the coating actually resembles a waffle.

Film thickness of the coating is preferably from about 0.1 to about 3 mils, more preferably from about 0.1 to 1.5 mils, and most preferably from about 0.2 to 1 mil.

The coating improves the durability of the balloon by making it more abrasion, scratch and puncture resistance. Furthermore, should an abrasion, scratch or puncture occur in the underlying balloon wall, the discontinuous nature of the outer protective coating prevents it from inflating on its own and pulling away from the balloon wall, which in turn prevents bulging or bubbles which can cause dissection of blood vessels or arteries. A particular problem with the formation of such balloons is the occurrence of what is referred to in the industry as "pinholes." Inflation medium escapes through these pinholes causing the outer coating to inflate on its own forming a bulge or bubble which can cause the dissection of a blood vessel of artery. The present invention overcomes such problems.

EXAMPLES

The following ingredients were utilized in preparing the coating composition for Example 1 and for Comparative Example A:

10% SMP-3510, polyurethane polymer available from Mitsubishi Heavy Industries, Ltd.

70% dimethylacetate (DMAC)

15% toluene

5% tetrahydrofuran (THF)

Example 1

The coating composition shown above was brushed on a dilatation balloon in a striped pattern. This pattern was accomplished by masking off sections of the balloon and brushing on the coating so that the masked sections had no coating. The coating was dried and the toluene, DMAC and THF were evaporated off leaving only the polyurethane, SMP-3510 on the balloon. The balloon, which had a pinhole in its wall, was then inflated. The pinhole was in the center of a coated section of balloon. The inflation medium flowed out of the pinhole and vented out of the sides of the coated section so that no aneurysm occurred in the coating.

FIG. 5 illustrates the coated balloon in its uninflated state. The pinhole is right of center and located beneath a coated section of the balloon. FIG. 6 illustrates the coated balloon in its inflated state. As can be seen from the illustration, the inflation medium is venting around the sides of the coating as desired. No aneurysm is formed in the coating.

Comparative Example A

A continuous coating of the composition shown above was brushed on a dilatation balloon. The coating was dried, evaporating off the toluene, DMAC and THF and leaving only the polyurethane, SMP-3510 on the balloon. The balloon had a pinhole in its wall, and upon inflation, a large bubble or aneurysm occurred in the coating as is shown in FIG. 7.

Example 2

A coating comprising a polyurethane polymer in a mixture of solvents available from Creative Materials under the tradename of CMI 118-43 was pad printed on a catheter balloon in a waffle pattern so as to eliminate the possibility of pinhole formation.

The invention claimed is:

1. A medical balloon insertable in the body, said medical device having a substantially uniform noncontinuous protective surface coating, the medical balloon is formed from a first polymer layer, the first polymer layer is exposed where the coating is noncontinuous.

2. The dilatation balloon of claim 1 wherein the first polymer layer is a thermoplastic.

3. The dilatation balloon of claim 2 wherein said coating is applied in the form of a waffle pattern, stripe pattern or a pattern having circular perforations.

4. The medical device of claim 1 wherein said coating is applied in a waffle pattern, stripe pattern or a pattern having circular perforations.

5. A dilatation balloon having improved durability formed from a thermoplastic polymer, said balloon having a noncontinuous protective coating, the balloon formed from a first polymer layer, wherein the first polymer layer is exposed where the protective coating is non-continuous.

6. The dilatation balloon of claim 5 wherein said balloon is formed from a polymer selected from the group consisting of polyethylene terephthalate, high density polyethylene, polyamides, polyether block amides, polycarbonates, stiff polyurethanes, and mixtures thereof.

7. The dilatation balloon of claim 5 wherein said coating comprises a polymeric material selected from the group consisting of thermoplastic polymeric and thermosetting polymeric materials.

8. The dilatation balloon of claim 5 wherein said coating comprises a polyurethane.

9. The dilatation balloon of claim 5 wherein said noncontinuous coating is selected from the group consisting of a waffle pattern, a stripe pattern and a pattern having circular perforations.

10. The dilatation balloon of claim 5 wherein said balloon is formed from a noncompliant material.

11. A medical device insertable in the body having a protective coating on a surface thereof, said coating being applied to said medical device in a substantially uniform discontinuous pattern, the medical device formed from a first polymer layer, the first polymer layer is exposed by the substantially uniform discontinuous pattern of the protective coating.

12. The medical device of claim 11 wherein said coating comprises a thermoplastic polymer, thermosetting polymer or mixture thereof.

13. The medical device of claim 11 wherein said medical device is a dilatation balloon.

14. The medical device of claim 13 wherein said coating is applied in the form of a waffle pattern, stripe pattern or a pattern having circular perforations.

* * * * *